United States Patent [19]

Freund et al.

[11] Patent Number: 5,084,060
[45] Date of Patent: Jan. 28, 1992

[54] APPARATUS FOR ENLARGING A VESSEL OR CLEARING OBSTRUCTIVE TISSUE FROM A VESSEL ACCORDING TO VESSEL COMPLIANCE

[75] Inventors: Robert F. Freund, Springboro; William C. M. Kelly, Beavercreek, both of Ohio

[73] Assignee: Freund Precision, Inc., Dayton, Ohio

[21] Appl. No.: 311,126

[22] Filed: Feb. 15, 1989

[51] Int. Cl.$^5$ ............................................. A61M 29/02
[52] U.S. Cl. ................................... 606/192; 606/194; 604/97; 604/100
[58] Field of Search ........................... 606/191–195, 606/27; 604/100, 95, 96, 97, 99

[56] References Cited

U.S. PATENT DOCUMENTS

| | | | |
|---|---|---|---|
| 3,834,394 | 9/1974 | Hunter et al. | 128/325 |
| 4,370,982 | 2/1983 | Reilly | 604/98 |
| 4,402,307 | 9/1983 | Hanson et al. | 604/95 X |
| 4,439,186 | 3/1984 | Kuhl | 604/99 |
| 4,446,867 | 5/1984 | Leveen et al. | 128/344 |
| 4,601,037 | 7/1986 | McDonald | 606/4 X |
| 4,651,738 | 3/1987 | Demer et al. | 128/344 |
| 4,655,749 | 4/1987 | Fischione | 604/98 |
| 4,697,574 | 10/1987 | Karcher et al. | 604/99 X |
| 4,706,670 | 11/1987 | Andersen et al. | 128/344 |
| 4,723,556 | 2/1988 | Sussman | 128/748 |
| 4,723,938 | 2/1988 | Goodin et al. | 604/99 |
| 4,758,223 | 7/1988 | Rydell | 604/98 |
| 4,777,951 | 10/1988 | Cribier et al. | 606/194 |
| 4,781,192 | 11/1988 | Demer | 606/195 |
| 4,815,472 | 3/1989 | Wise et al. | 128/675 |
| 4,899,741 | 2/1990 | Bentley et al. | 606/27 |
| 5,004,472 | 4/1991 | Wallace | 604/100 |
| 5,009,662 | 4/1991 | Wallace et al. | 606/192 |
| 5,021,046 | 6/1991 | Wallace | 604/97 |

OTHER PUBLICATIONS

*Intelliflator* TM by Merit Medical Systems, Inc. Advertisement.
*In Vivo Assessment of Vascular Dilatation During Percutaneous Transluminal Coronary Angioplasty,* by Jain et al., American Journal of Cardiology 1987; 60:988-992.
*Clinical Trial of the Disposable Transducer Catheter,* by Cha et al., Catheterization and Cardiovascular Diagnosis 1988; 14:63-68.
*Ballooning-Out Gets Mostly Good Marks,* by Edwards, Science News, May 16, 1987, p. 311.

Primary Examiner—Robert A. Hafer
Assistant Examiner—Kerry Owens
Attorney, Agent, or Firm—Nydegger & Associates

[57] ABSTRACT

An apparatus for clearing obstructive tissue from a body vessel or enlarging the lumen of the vessel comprises a balloon catheter which is insertable into the vessel of a patient to position the balloon in the area to be enlarged or against the obstructive tissue. A syringe is provided to incrementally inflate the balloon with a reasonably incompressible fluid to apply pressure against the inside of the vessel for opening the vessel. A pressure transducer senses fluid pressure in the balloon and an interval timer is used to monitor the rate of change in this fluid pressure. The rates of change in fluid pressure between the incremental inflations are monitored to determine vessel compliance, to determine when the stenosis is cleared, and to indicate when the vessel is stretched to, or near, its elastic limit.

16 Claims, 2 Drawing Sheets

APPARATUS FOR ENLARGING A VESSEL OR CLEARING OBSTRUCTIVE TISSUE FROM A VESSEL ACCORDING TO VESSEL COMPLIANCE

FIELD OF THE INVENTION

This invention relates generally to apparatus and methods for applying pressure to the inside surface of a vessel to enlarge the vessel or open a stenosis in the vessel. More particularly, the present invention pertains to an apparatus and methods of use for monitoring and controlling the application of pressure to the inside surface of a vessel during selectable time intervals. The apparatus and methods of the present invention are particularly, but not exclusively, useful for enlarging or clearing a stenosis from vessels such as coronary arteries, peripheral arteries, fallopian tubes, and urethral passages.

BACKGROUND OF THE INVENTION

Percutaneous transluminal coronary angioplasty (PTCA) procedures are becoming well known in the medical field as an efficacious way to clear a stenosis from a blood vessel. In general, PTCA procedures require the application of pressure against the stenotic segment of a vessel or artery until the stenosis is sufficiently compromised to permit improved fluid flow through the vessel. Typically, PTCA is accomplished using a balloon catheter to dilate the stenotic segment of the vessel. The result is that the obstructive tissue causing the stenosis is either stretched, compacted or cracked to clear the obstruction.

Not surprisingly, several devices have been proposed which are useful for PTCA procedures. Typical of such devices is the dilatation catheter disclosed in U.S. Pat. No. 4,706,670 to Anderses et al. Although these devices can be effective for clearing obstructive tissue from a vessel, their use requires a great deal of intuitive skill to obtain the desired result while avoiding or minimizing damage to the vessel in the process.

Unfortunately, the application of excessive pressure in the stenotic segment can cause unnecessary damage to the vessel. Further, it is believed that a vessel which has been excessively stretched is more likely to restenose than one which has not been subjected to such stretching. Nevertheless, sufficient force must be applied to compromise the stenosis. The amount of force required to compromise a stenosis is, however, not easily determined and will vary from patient to patient. Also, the amount of force required will vary according to the characteristics of the obstructive tissue being compromised. Furthermore, since PTCA procedures typically require successive uses of increasingly larger balloons with consequent additional trauma to the patient, it is desirable to know when the PTCA procedure has either been effective or is likely to start seriously damaging the vessel. Thus, proper control of the PTCA procedure is essential.

One reported PTCA procedure, employing a balloon catheter, uses comparative readings of fluid pressure and fluid volume in the balloon to determine the state of the stenotic segment being compromised. This procedure, as set forth in the article, "In vivo Assessment of Vascular Dilatation During Percutaneous Transluminal Coronary Angioplasty" by Jain et al., Vol. 60, *The American Journal of Cardiology*, November 1987, suggests that the pressure-volume readings of a balloon catheter in response to the resistance of a stenosis is predictable according to the characteristics of the stenosis and the consequent mechanism by which the stenosis is compromised. Specifically, this procedure is used to observe and identify the mechanical behavior of the dilatation process in comparison with an expected response. U.S. Pat. No. 4,651,738 to Demer et al. for an invention entitled "Method and Device for Performing Transluminal Angioplasty" also discusses the use of this same pressure-volume relationship to observe PTCA dilatation mechanisms.

The present invention recognizes that, though pressure-volume observation can tell how the stenosis is reacting to PTCA, pressure-volume information alone does not provide a complete picture of the actual situation. Specifically, pressure-volume information overlooks vessel compliance as a function of pressure and time (i.e. resilience of the vessel). It happens in PTCA procedures, however, that information concerning vessel compliance can be crucial for determining when stenosis clearance has occurred and, subsequently, whether to continue dilatation. For example, if the vessel is at or near its elastic limit (i.e. there is little, if any, vessel compliance) then the PTCA procedure should be stopped because further stretching of the vessel will cause damage and be of minimal benefit. On the other hand, even though it may appear that dilatation has been successful, if there is still vessel compliance, it may be advantageous to continue stretching the vessel to more effectively open the stenosis.

The present invention recognizes that PTCA procedures are optimally effective when the full range of vessel compliance is utilized. Further, the present invention recognizes that by monitoring the pressure drop and the time rate of change of fluid pressure in a balloon catheter, rather than relying solely on pressure-volume information, the compliance of the vessel segment surrounding the balloon can be determined. Further still, the present invention recognizes that PTCA can be efficaciously accomplished using only information pertaining to the pressure drop and the rate of change of fluid pressure with time ($\Delta p/\Delta t$) in a balloon catheter. The present invention also recognizes that $\Delta p/\Delta t$ information is useful in a variety of medical procedures which require vessel dilation.

Although the above discussion has focused on PTCA procedures, it is to be appreciated that other medical procedures may also benefit from the present invention. Indeed, the present invention recognizes that whenever a body vessel is to be dilated by a balloon catheter, information pertaining to the rate of change of fluid pressure with time ($\Delta p/\Delta t$) in the balloon can be useful. This is so regardless of the vessel involved.

In light of the above, it is an object of the present invention to provide an apparatus for use in vessel dilatation procedures (including PTCA) which displays the change of fluid pressure in a balloon catheter over a selected period of time to indicate vessel compliance. Another object of the present invention is to provide an apparatus which can effectively indicate whether further vessel dilatation during a medical procedure should be avoided. Yet another object of the present invention is to provide an apparatus for use in vessel dilatation procedures which chronicles fluid pressure variations in a balloon catheter during the procedures. Still another object of the present invention is to disclose a method for using the time rate of change of fluid pressure in a balloon catheter to determine vessel compliance during vessel dilatation procedures. Another object of the present invention is to provide an apparatus for performing vessel dilatation procedures that is simple to use, relatively easy to manufacture and cost effective for its intended purposes.

SUMMARY OF THE INVENTION

In accordance with the present invention, an apparatus for clearing a stenosis from a vessel of a patient or enlarging the lumen of a vessel comprises a balloon catheter which can be inserted into the vessel of a patient and positioned with the balloon against the stenosis or in the area to be enlarged. A syringe, connected in fluid communication with the balloon catheter, is operable to incrementally inflate the balloon with a reasonably incompressible fluid and apply pressure against the inside of the vessel. A pressure transducer is mounted on the syringe to sense fluid pressure in the balloon and transmit pressure readings for display on the screen of a monitor. The monitor also displays appropriate time information to determine rates of fluid pressure change in the balloon during selected intervals of time. A printer may be incorporated with the monitor to chronicle a time record of pressure levels during the procedure.

In the operation of the apparatus of the present invention, the balloon of the balloon catheter is first positioned against the stenosis or the area to be enlarged. The syringe is then manipulated to introduce fluid into the catheter until a predetermined pressure level in the balloon is attained. A volume of fluid is displaced into the catheter and is then held for an interval of time and the fluid pressure change in the balloon during this interval is monitored to determine vessel compliance. If there is appropriate vessel compliance, the pressure in the balloon is incrementally advanced to a higher level and vessel compliance is again monitored. Additional iterations of this procedure are accomplished until either total balloon inflation time reaches a prescribed limit, the stenosis has been cleared, or the optimal elastic limit of the vessel is reached. In the event total occlusion time reaches the prescribed limit, the balloon should be deflated to allow adequate coronary perfusion. The entire procedure may be subsequently performed until the stenosis has been cleared, the vessel has been enlarged or the elastic limit of the vessel is reached.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENT

Figure 1:
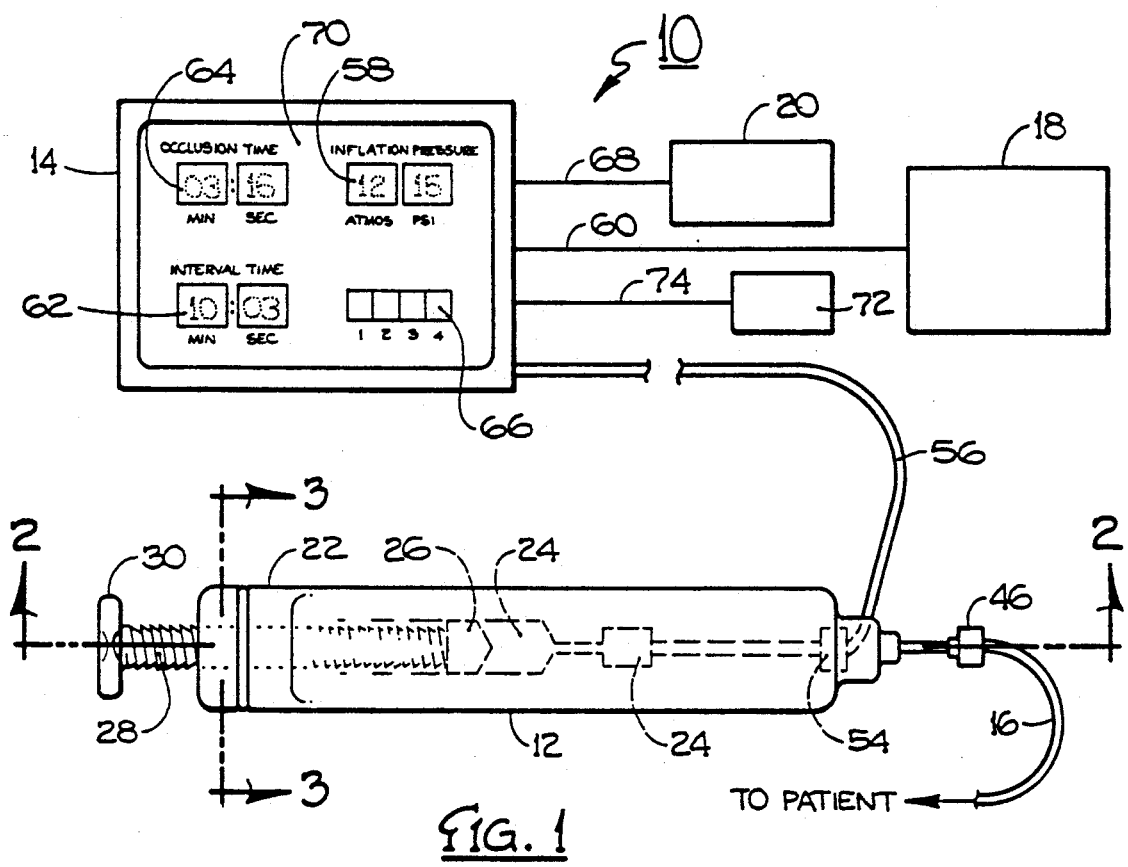
FIG. 1 is a schematic drawing of the components of the system for determining vessel compliance in conjunction with angioplasty procedures.

Referring initially to FIG. 1, the apparatus for performing angioplasty procedures in accordance with the present invention is shown schematically and generally designated 10. As shown, apparatus 10 comprises in combination a syringe 12, a display monitor 14 and a balloon catheter 16. Additionally, apparatus 10 includes a computer 18 for compiling and sorting data during an angioplasty procedure and a printer 20 for chronicling selected portions of this data.

Figure 2:
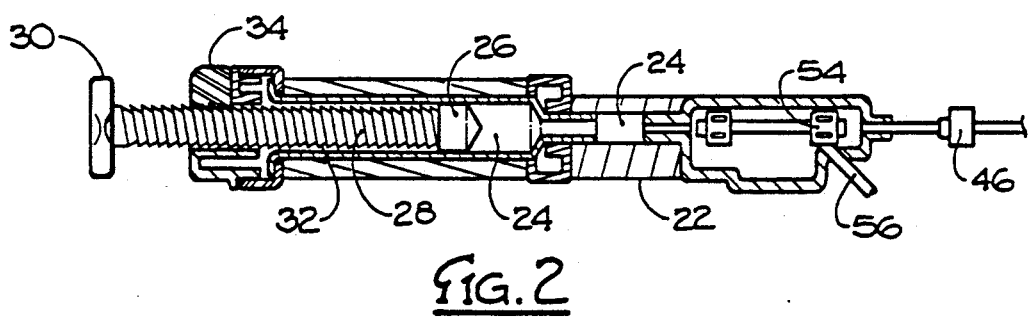
FIG. 2 is a cross-sectional view of the syringe of the system as seen along the line 2—2 in FIG. 1.
Figure 3A:
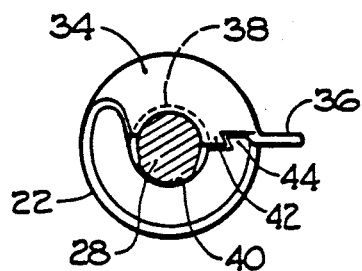
FIG. 3A is a cross-sectional view of the syringe of the system as seen along the line 3—3 in FIG. 1.

As shown in FIG. 1, syringe 12 comprises a body 22 which is formed with a fluid chamber 24. A plunger 26 is disposed in chamber 24 and is connected to threaded shaft 28 to be reciprocally advanced or withdrawn in chamber 24 according to the movement of shaft 28. As best seen in FIG. 2, a handle 30 is attached to the end of shaft 28 opposite plunger 26 and shaft 28 is formed with a helical thread 32 between handle 30 and plunger 26. A connector 34 is pivotally attached to syringe 12 and operatively engages with shaft 28 when connector 34 is held in its engaged position as shown in FIG. 3A. In accordance with this combination, i.e. when connector 34 is configured as shown in FIG. 3A, the movement of plunger 26 into chamber 24 is accomplished by rotating the handle 30 to advance shaft 28 into chamber 24.

The withdrawal of plunger 26 from fluid chamber 24 may be accomplished in either of two ways. First, with connector 34 in its engaged position as shown in FIG. 3A, handle 30 can be rotated to withdraw shaft 28 and plunger 26 from chamber 24. Alternatively, connector 34 can be disengaged from shaft 28 to permit the pulling of shaft 28 and plunger 26 from chamber 24 for a relatively rapid withdrawal of shaft 28 and plunger 26 therefrom. This disengagement of connector 34 from shaft 28 will be best appreciated by cross-referencing FIGS. 3A and 3B wherein connector 34 is respectively shown in its engaged and disengaged positions. By comparing FIG. 3A with FIG. 3B, it will be seen that connector 34 is pivotally attached to body 22 of syringe 12 by any means well known in the art and that connector 34 is formed with a lip 42. Further, body 22 is formed with a flange 44 which interlocks with lip 42 when connector 34 is in the engaged position shown in FIG. 3A. Also, connector 34 is formed with an integral tab 36 which extends therefrom and which can be used to manipulate connector 34 between the engaged and disengaged positions.

Figure 3B:
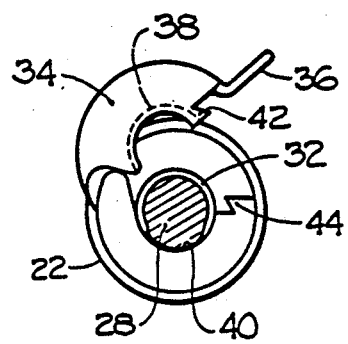
FIG. 3B is an alternate configuration of the syringe as shown in FIG. 3A.

For its operative engagement with shaft 28, connector 34 is formed with threaded portion 38 (shown in phantom) which is engageable with threads 38 of shaft 28. This occurs when connector 34 is in its engaged position and shaft 28 is positioned in opening 40 of body 22. Consequently, shaft 28 either advances or withdraws plunger 26 within fluid chamber 24 according to the direction in which handle 30 is rotated. On the other hand, when lip 42 is disengaged from flange 44 by the manipulation of tab 36 to move connector 34 into its disengaged position as shown in FIG. 3B, the combination of handle 30, shaft 28 and plunger 26 can be freely reciprocated within chamber 24. Consequently, plunger 26 may be rapidly withdrawn from chamber 24, if necessary.

Referring back to FIG. 1 and FIG. 2, it will be seen that fluid chamber 24 extends through body 22 and is in fluid communication with a fitting 46 which is attached to apparatus 10 at the end of body 22 opposite handle 30. A balloon catheter 16, which may be any of several types that are commercially available and well known in the pertinent art, is attached in fluid communication with fitting 46. Accordingly, advancement of plunger 26 into chamber 24 will dispense fluid through fitting 46 and into balloon catheter 16. For purposes of the present invention, it is to be appreciated that an incompressible or reasonably incompressible fluid (i.e. a liquid) is to be used as the fluid element.

Figure 4:
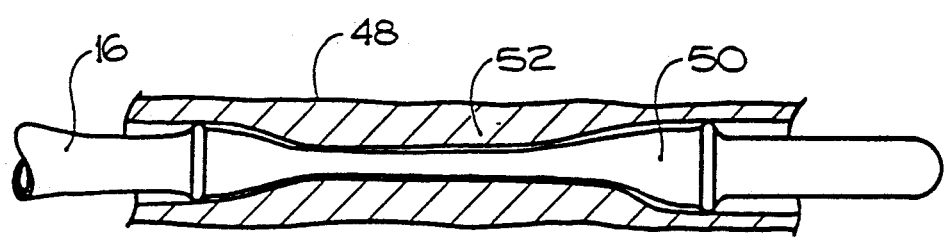
FIG. 4 is a cross-sectional view of the balloon portion of a balloon catheter positioned against a stenosis in an artery.

As best appreciated with reference to FIG. 4, during a vessel dilatation such as is accomplished during a PTCA procedure, balloon catheter 16 is positioned relative to the stenotic segment of a vessel 48 with the balloon 50 against, or across, the stenosis 52 to be compromised. As mentioned above, balloon catheter 16 and its associated balloon 50 are well known, commercially available products. Thus, catheter 16 and its associated balloon 50 may be chosen according to the needs and desires of the operator.

In FIG. 2, it will be seen that a pressure transducer 54 is mounted on body 22. This transducer 54 is operatively placed in contact with fluid in chamber 24 for sensing fluid pressure in the chamber 24. It will be appreciated that when so positioned, transducer 54 effectively senses fluid pressure in chamber 24 as well as those components of apparatus 10 which are in fluid communication with chamber 24 (i.e. balloon catheter 16 and balloon 50). For purposes of the present invention, pressure transducer 54 may be of any type well known in the pertinent art.

In accordance with the present invention, pressure transducer 54 is electrically connected to monitor 14 via cable 56. With this connection, electrical signals produced by transducer 54 which are indicative of fluid pressure in balloon 50 are transmitted to monitor 14 and visually shown thereon as pressure display 58. Simultaneously, these signals are also transmitted via electrical connection 60 to computer 18 where they are stored and used in accordance with established programs which involve pressure related parameters. A clock 61 is included with computer 18 for the purpose of comparing changes in fluid pressure within balloon 50 over time intervals which may be selected by the operator. Moreover, insofar as the present invention is concerned, the concept of time may be either real time, or processor time, or any other arbitrarily established interval. In either case, a time signal generated by the clock 61 may be transmitted via electrical connection 60 to monitor 14 and visually shown thereon as time display 62. Using time and pressure information from computer 18, monitor 14 may also show additional information such as total occlusion time 64 and pressure rate changes 66.

An electrical connection 68 is provided between monitor 14 and printer 20 to chronicle pressure and time data according to the desires of the operator. Additionally, it is to be appreciated that monitor 14 may comprise a screen 70 that is a standard cathode ray tube which is part of a fluoroscope. Thus, pressure display 58, time display 62 and any other desired information may be shown on screen 70 using combinations of electronic components all well known in the pertinent art. Importantly, well known technology also permits the use of screen 70 for fluoroscopic viewing of the position of balloon catheter 16 within vessel 48. Therefore, in order that the operator may effectively view both the position of catheter 16 within vessel 48 and the corresponding pressure-time values for balloon 50 on screen 70, with minimum diversion of attention, a foot pedal 72 is electrically connected via electrical connection 74 to switch modes for monitor 14. In one mode, the position of balloon catheter 16 is shown on screen 70. In the other mode, the pressure-time information relative to balloon 50 is shown on screen 70.

Though not shown, it will be appreciated that audible alarms may be included in apparatus 10 to indicate the attainment of preset values for time or pressure. These alarms may be activated by computer 18 in accordance with preprogrammed instructions and may be incorporated into apparatus 10 in any manner well known in the pertinent art.

OPERATION

In the operation of apparatus 10, balloon catheter 16 is inserted into a vessel 48 of a patient with balloon 50 positioned in the stenotic segment of vessel 48. Specifically, balloon 50 is positioned in vessel 48 in a manner which establishes direct contact between balloon 50 and stenosis 52. With balloon catheter 16 in position, tab 36 is manipulated to engage connector 34 with threaded shaft 28 (i.e. connector 34 is moved to its engaged position). Handle 30 is then rotated in a direction which will advance threaded shaft 28 and its associated plunger 26 into fluid chamber 24. This advancement of plunger 26 dispenses reasonably incompressible fluid in chamber 24 through fitting 46 and into balloon catheter 16. As a consequence, balloon 50 is expanded. With the expansion of balloon 50, stenosis 52 reacts against balloon 50 to increase fluid pressure within chamber 24 according to the ability of the stenosis 52 in vessel 48 to resist expansion of the balloon 50. Since pressure transducer 54 is in fluid communication with the incompressible fluid in chamber 24, transducer 54 establishes an electrical signal corresponding to the fluid pressure within chamber 24 and balloon 50. Consequently, the signal generated by pressure transducer 54 is also indicative of the resistance vessel 48 gives to the expansion of balloon 50. By way of cable 56, pressure signals are transmitted from transducer 54 to monitor 14 and subsequently, to computer 18 by way of electrical connection 60. During the operation of apparatus 10, a clock (not shown), which is associated with computer 18, provides a time basis against which pressure variations in balloon 50 may be evaluated over a preselected interval.

Figure 5A:
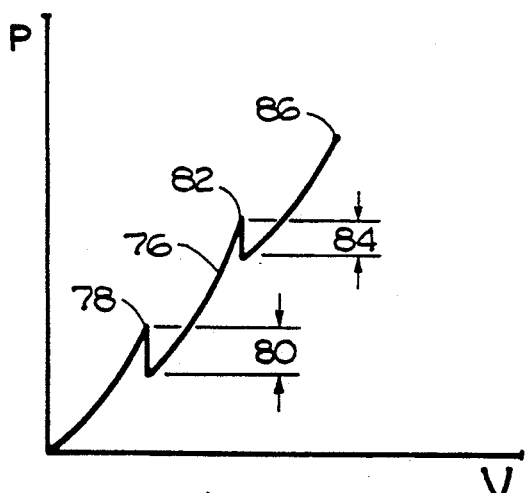
FIG. 5A is a model graph of the fluid pressure in a balloon catheter relative to the volume of fluid in the catheter during an angioplasty procedure.
Figure 5B:
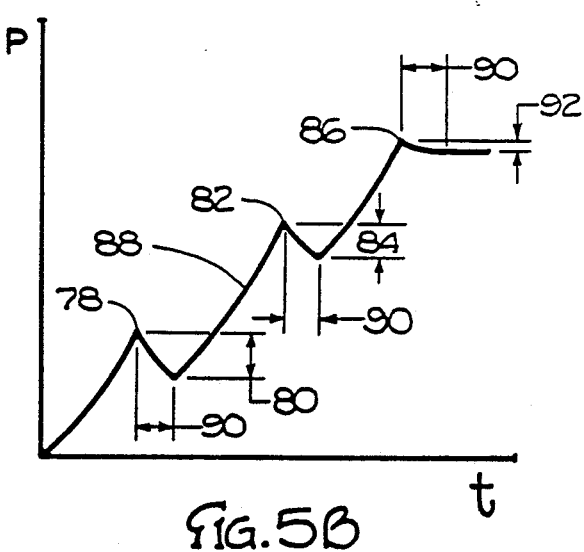
FIG. 5B is a model graph of the fluid pressure in a balloon catheter, corresponding to the pressure variation shown in FIG. 5A, relative to time.

The actual consequences of the operation of apparatus 10 can perhaps be best seen by reference by FIGS. 5A and 5B. First, by considering FIG. 5A it is to be appreciated that as plunger 26 is advanced into syringe 12 balloon 50 will expand, and the resistance of vessel 48 will cause an increase in fluid pressure within chamber 24. Specifically, this initial increase in pressure is indicated on pressure-volume curve 76 in FIG. 5A as an advancement from the origin of the curve to the point 78. As indicated above, point 78 on pressure-volume curve 76 can be preselected. It happens that, with plunger 26 held stationary at the pressure corresponding to point 78 on curve 76, the volume of fluid in balloon 50 will remain constant in accordance with the stationary position of plunger 26. The fluid pressure in balloon 50, however, may actually change. As shown in FIG. 5A, the pressure is shown to change by an amount equivalent to a pressure change 80. Subsequently, an increase of the fluid volume within balloon 50, by advancing plunger 26 into chamber 24, will cause a pressure increase up to the point 82. Again, the pressure corresponding to point 82 may be preselected by the operator. If the plunger 26 is again held stationary, the volume of reasonably incompressible fluid within balloon 50 will remain constant while another pressure change 84 may occur. As long as decreasing pressure changes occur while plunger 26 is stationary, subsequent increases in pressure may be accomplished by further advancements of plunger 26 into chamber 24 until a pressure is attained such as indicated by point 86 where the resultant decrease in pressure after plunger 26 is stopped is minimal.

In accordance with the present invention, the information obtained by comparing pressure and volume, as relied on by others and indicated in FIG. 5A, does not use all of the available information and consequently is an incomplete picture of the actual situation. More specifically, as shown in FIG. 5B, the present invention recognizes that pressure changes 80 and 84 with time are indicative of the compliance of the vessel 48. Importantly, as long as the vessel 48 is compliant, it can withstand additional stretching. Thus, it will be appreciated that when vessel 48 is stretched to the point where its elastic limit has been met or exceeded, further increases in pressure will only damage vessel 48 and may even increase its tendency to restenose. More specifically, the present invention uses these factors to advantage by comparing pressure with time.

In FIG. 5B, fluid pressure at points 78, 82 and 86 are the same as at corresponding points 78, 82 and 86 on pressure-volume curve 5A. In FIG. 5B, however, they have been plotted against time to create a pressure-time curve 88. With reference now to curve 88, it will be appreciated that once plunger 26 has been advanced into chamber 24 to increase fluid pressure within the balloon 50 to the point 78, the fact that a pressure change 80 occurs within a preselected time interval 90 can be of importance. Specifically, with incremental advances in pressure, it will be noted that decreasing pressure changes over a set time interval 90 after the pressure advancing is stopped will occur so long as vessel 48 is compliant (i.e. it retains some elasticity). Consequently, it will be seen in FIG. 5B that after an advance in fluid pressure to point 82, while the volume of fluid in balloon 50 is held constant, there is a pressure change 84 over interval 90. Subsequently, an advance in pressure to point 86 results in a pressure change of 92 over the interval 90 even though the fluid volume in balloon 50 is constant over the interval 90. In accordance with the present invention, the operator has the ability to monitor pressure changes 80, 84 and 92 over intervals 90 and to determine at which point the pressure change is significantly small as to indicate the lack of further compliance by vessel 48. It will be appreciated by the skilled artisan that at the point when vessel 48 has reached its elastic limit (i.e. compliance with increases in pressure in balloon 50 have been obviated), the PTCA procedure should be stopped. With this procedure, the exact nature of the stenosis is only of secondary importance. Vessel compliance is of primary concern and is monitored to insure that stretching of the stenosis is accomplished within the physical limitations imposed by vessel 48. It is to be understood that inherent compliance of the balloon/catheter system ($\Delta p/\Delta t$) is calibrated and compensated for in calculating vessel compliance.

While the particular apparatus for enlarging a vessel or clearing obstructive tissue as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. An apparatus for applying pressure to the inside of a vessel during selected intervals to enlarge the lumen of the vessel which comprises:
    a fluid inflatable means positionable inside the vessel;
    means connected in fluid communication with said inflatable means for introducing fluid to said inflatable means to apply pressure against the vessel;
    a transducer operatively connected with said inflatable means for generating a signal indicative of the fluid pressure in said inflatable means; and
    automatic means for determining a time interval between incremental inflations of said inflatable means;
    a monitor connected with said transducer and with said time interval determining means and having a screen means for displaying said transducer pressure signal and as a function of said interval signal.

2. An apparatus as recited in claim 1 wherein said inflatable means is a balloon catheter.

3. An apparatus as recited in claim 2 wherein said means for introducing fluid to said inflatable means is a syringe which comprises:
    a fluid chamber in fluid communication with said balloon catheter; and
    a plunger threadably advanceable into said chamber to introduce fluid into said balloon catheter.

4. An apparatus as recited in claim 3 wherein said transducer is mounted on said syringe in fluid contact with fluid in said chamber.

5. An apparatus as recited in claim 4 wherein said monitor comprises means for directly comparing said transducer pressure signal with said interval signal.

6. An apparatus as recited in claim 5 further comprising a recorder electrically connected with said monitor to chronicle variations of said transducer pressure signal during selected time intervals.

7. An apparatus for dilating a body vessel which comprises:
    an inflatable balloon positionable inside the vessel;
    means in fluid communication with said balloon for incrementally inflating said balloon with a fluid;
    automatic means for establishing a time interval between incremental inflations;
    means mounted on said inflation means for sensing changes in fluid pressure in said balloon during said time interval between incremental inflations; and
    means operatively connected with said sensing means for indicating when changes in fluid pressure fall below a selected level during said interval.

8. An apparatus as recited in claim 7 wherein said balloon is mounted on a balloon catheter.

9. An apparatus as recited in claim 8 wherein said inflating means is a syringe which comprises:
    a fluid chamber in fluid communication with said balloon catheter; and a plunger advanceable into said chamber to introduce fluid into said balloon catheter.

10. An apparatus as recited in claim 9 wherein said sensing means is a transducer for generating an electrical signal which is indicative of fluid pressure in said balloon.

11. An apparatus as recited in claim 10 further comprising a clock for generating an interval signal, said clock being operatively connected with said indicating means.

12. An apparatus as recited in claim 11 wherein said indicating means is a monitor connected with said transducer and with said clock and having a screen for displaying said transducer pressure signal and said interval signal.

13. An apparatus as recited in claim 12 wherein said monitor comprises means for directly comparing said transducer pressure signal with said interval signal.

14. An apparatus as recited in claim 13 further comprising a recorder electrically connected with said monitor to chronicle variations of said transducer pressure signal during selected time intervals.

15. A method for using a balloon catheter system to clear obstructive tissue from the lumen of a body vessel which automatically records, processes and displays data comprising the steps of:
(a) positioning the expandable balloon of the balloon catheter in the lumen across the obstruction;
(b) incrementally increasing the fluid pressure in the system by mechanical means to inflate the balloon and establish a new base pressure after each incremental increase in pressure;
(c) establishing an interval signal which begins when each new base pressure is attained;
(d) measuring fluid pressure changes from the base pressure during the interval; and
(e) deflating the balloon when changes from the base pressure do not exceed a prescribed level during the interval.

16. A method for using a balloon catheter system to enlarge the lumen of a body vessel which atomically records, processes, and displays data comprising the steps of:
(a) positioning the expandable balloon of the balloon catheter in the lumen;
(b) incrementally increasing the fluid pressure in the system by mechanical means to inflate the balloon and establish a new base pressure after each incremental increase in pressure;
(c) establishing an interval signal which begins when each new base pressure is attained;
(d) measuring fluid pressure changes from the base pressure during the interval; and
(e) deflating the balloon when changes from the base pressure do not exceed a prescribed level during the interval.

* * * * *